United States Patent
Cybulsky et al.

(10) Patent No.: US 10,241,091 B2
(45) Date of Patent: Mar. 26, 2019

(54) DIAGNOSIS OF THERMAL SPRAY GUN IGNITION

(71) Applicants: Rolls-Royce Corporation, Indianapolis, IN (US); Mark Hudson, Mickle Trafford (GB)

(72) Inventors: Michael Cybulsky, Indianapolis, IN (US); Raymond J. Sinatra, Indianapolis, IN (US); Roy Peter McIntyre, Derby (GB); Taylor K. Blair, Blacksburg, VA (US); Gary Pickrell, Blacksburg, VA (US); Romesh Batra, Blacksburg, VA (US); Mark Hudson, Chester (GB)

(73) Assignees: Rolls-Royce Corporation, Indianapolis, IN (US); Rolls-Royce PLC, London (GB); Turbine Surface Technologies Limited, Derby (GB); Virginia Polytechnic Institute & State University, Blacksburg, VA (US)

( * ) Notice: Subject to any disclaimer, the term of this patent is extended or adjusted under 35 U.S.C. 154(b) by 38 days.

(21) Appl. No.: 15/172,441

(22) Filed: Jun. 3, 2016

(65) Prior Publication Data

US 2016/0356747 A1    Dec. 8, 2016

Related U.S. Application Data

(60) Provisional application No. 62/171,073, filed on Jun. 4, 2015.

(51) Int. Cl.
    *G01N 29/46* (2006.01)
    *G01M 99/00* (2011.01)
    (Continued)

(52) U.S. Cl.
    CPC ............. *G01N 29/46* (2013.01); *B05B 7/226* (2013.01); *B05B 12/004* (2013.01); *G01N 29/14* (2013.01);
    (Continued)

(58) Field of Classification Search
    CPC ................... G01N 29/46; G01N 29/14; G01N 2291/02836; G01N 2291/02425; B05B 12/004; B05B 7/226
    See application file for complete search history.

(56) References Cited

U.S. PATENT DOCUMENTS

| 2,361,458 A | 10/1944 | Converse |
| 3,580,092 A | 5/1971 | Scarpa |

(Continued)

FOREIGN PATENT DOCUMENTS

| EP | 0481382 A1 | 4/1992 |
| EP | 1036856 A1 | 9/2000 |

(Continued)

OTHER PUBLICATIONS

Kovacevic et al., On-line monitoring of the electric arc-spraying process based on acoustic signatures, 1995.*

(Continued)

*Primary Examiner* — Stephanie E Bloss
*Assistant Examiner* — Mohammad K Islam
(74) *Attorney, Agent, or Firm* — Shumaker & Sieffert, P.A.

(57) ABSTRACT

An example system includes at least one acoustic sensor configured to generate at least one acoustic data signal indicative of an acoustic signal generated by a thermal spray system comprising a flowstream, a computing device, and an acoustic data signal processing module operable by the computing device to determine an ignition attribute of the thermal spray system by analyzing at least a pre-ignition (Continued)

window of the acoustic data signal received by the computing device.

16 Claims, 4 Drawing Sheets

(51) Int. Cl.
B05B 12/00 (2018.01)
B05B 7/22 (2006.01)
B05B 7/16 (2006.01)
G01N 29/14 (2006.01)

(52) U.S. Cl.
CPC .............. *G01N 2291/02425* (2013.01); *G01N 2291/02836* (2013.01)

(56) References Cited

U.S. PATENT DOCUMENTS

| | | |
|---|---|---|
| 4,550,615 A | 11/1985 | Grant |
| 4,586,386 A | 5/1986 | Hollstein et al. |
| 4,613,259 A | 9/1986 | Packer et al. |
| 4,621,519 A | 11/1986 | Phillips |
| 4,811,605 A | 3/1989 | Nadeau et al. |
| 4,850,229 A | 7/1989 | Phillips |
| 4,856,321 A | 8/1989 | Smalling et al. |
| 4,905,897 A | 3/1990 | Rogers et al. |
| 5,101,774 A | 4/1992 | Marziale et al. |
| 5,180,921 A | 1/1993 | Moreau et al. |
| 5,455,868 A | 10/1995 | Sergent |
| 5,654,797 A | 8/1997 | Moreau et al. |
| 5,757,498 A | 5/1998 | Klein, II et al. |
| 5,912,471 A | 6/1999 | Schutz |
| 5,928,731 A | 7/1999 | Yanagida et al. |
| 5,986,277 A | 11/1999 | Bourque et al. |
| 6,014,447 A | 1/2000 | Kohnen et al. |
| 6,185,153 B1 | 2/2001 | Hynes et al. |
| 6,437,694 B1 | 8/2002 | Lee |
| 6,438,239 B1 | 8/2002 | Kuchen |
| 6,507,023 B1 | 1/2003 | Parham et al. |
| 6,684,702 B2 | 2/2004 | Ziada |
| 6,853,951 B2 | 2/2005 | Jarrell et al. |
| 6,940,409 B1 | 9/2005 | Green |
| 6,988,857 B2 | 1/2006 | Kroemmer et al. |
| 7,034,244 B2 | 4/2006 | Matus |
| 7,043,069 B1 | 5/2006 | Heinrich et al. |
| 7,114,889 B2 | 10/2006 | Kanou et al. |
| 7,278,294 B2 | 10/2007 | Giles et al. |
| 7,290,450 B2 | 11/2007 | Brown et al. |
| 7,311,004 B2 | 12/2007 | Giles |
| 7,389,278 B2 | 6/2008 | Unsworth et al. |
| 7,499,836 B1 | 3/2009 | Mooney |
| 7,665,348 B2 | 2/2010 | Giles |
| 7,802,687 B2 | 9/2010 | Fritz et al. |
| 7,881,884 B2 | 2/2011 | Perry et al. |
| 7,891,315 B2 | 2/2011 | Barbezat |
| 8,121,588 B2 | 2/2012 | Gottlieb |
| 8,193,942 B2 | 6/2012 | White et al. |
| 8,231,310 B2 | 7/2012 | Sanwald |
| 8,250,907 B2 | 8/2012 | Giles |
| 8,542,124 B2 | 9/2013 | Timm |
| 9,062,682 B2 | 6/2015 | Loose et al. |
| 9,099,074 B1 | 8/2015 | Lucon et al. |
| 9,709,466 B2 | 7/2017 | Kwon et al. |
| 2002/0153117 A1 | 10/2002 | Allor et al. |
| 2003/0087040 A1 | 5/2003 | Ladentin |
| 2004/0030524 A1 | 2/2004 | Jarrell et al. |
| 2005/0011278 A1 | 1/2005 | Brown et al. |
| 2005/0041238 A1 | 2/2005 | Ludviksson et al. |
| 2006/0071666 A1 | 4/2006 | Unsworth et al. |
| 2007/0264439 A1 | 11/2007 | Abdullahi et al. |
| 2007/0279235 A1 | 12/2007 | Davis et al. |
| 2008/0184793 A1 | 8/2008 | Mauchle et al. |
| 2008/0189057 A1 | 8/2008 | Perry et al. |
| 2009/0068978 A1 | 3/2009 | Gottlieb |
| 2010/0071616 A1 | 3/2010 | Mauchle et al. |
| 2010/0132439 A1 | 6/2010 | Giles |
| 2011/0005420 A1 | 1/2011 | Fullerton |
| 2011/0118998 A1 | 5/2011 | Loose et al. |
| 2011/0308812 A1 | 12/2011 | Bullen |
| 2012/0037074 A1 | 2/2012 | Outland |
| 2013/0243535 A1 | 9/2013 | Volonte et al. |
| 2014/0010968 A1 | 1/2014 | Prest et al. |
| 2014/0072125 A1 | 3/2014 | Cohn et al. |
| 2014/0113840 A1 | 4/2014 | Margalit et al. |
| 2014/0200837 A1 | 7/2014 | Blair et al. |
| 2015/0362418 A1 | 12/2015 | Newton et al. |
| 2016/0354796 A1 | 12/2016 | Cybulsky et al. |
| 2016/0356747 A1 | 12/2016 | Cybulsky et al. |

FOREIGN PATENT DOCUMENTS

| | | |
|---|---|---|
| EP | 1205748 A1 | 5/2002 |
| EP | 1336841 A2 | 8/2003 |
| EP | 3128321 A1 | 2/2017 |
| WO | 2005085489 A1 | 9/2005 |
| WO | 2014110486 A1 | 7/2014 |

OTHER PUBLICATIONS

Rat et al, Acoustic signature analysis of the interaction between a dc plasma jet and a suspension liquid jet, 2009.*
Faisal et al., Application of acoustic emission for monitoring the HVOF thermal spraying process, 2006.*
Braeuel et al., An Acoustic Method for the Detection of Defects in the Nozzle of Plasma Cutting Torches, IEEE, 1987.*
Xi, et al., "Monitoring of Nozzle Wear during Plasma Spray," Thermal Spray 1997: A United Forum for Scientific and Technological Advances, ASM International., Sep. 15-18, 1997.
Lenain et al., "New Approaches of the Forecast of the Aging of Plasma Jet Nozzle in Industrial Settings of Thermal Spraying," Sep. 23, 2011, University of Limoges; hal.archives-overtes.fr. 20 pp.
Leblanc et al., Long Term Stability of Plasma Spraying: Study of the Evolution of the In-Flight Particle State Coating Microstructure, Voltage and Acoustic Signatures, In Tagungsband Conference Proceedings., Sep. 2002, 7 pp.
Rigot, "Contribution of the study of the electrode erosion in dc plasma spray torches through the on-line following of voltage and sound signals," Nov. 2003 University of Limoges, 3 pp.
U.S. Appl. No. 15/172,362, filed by Cybulsky et al. filed Jun. 3, 2016.
Kanta et al., "Artificial Neural Networks vs. Fuzzy Logic: Simple Tools to Predict and Control Complex Processes—Application to Plasma Spray Processes," Journal of Thermal Spray Technology, vol. 17, No. 3, Sep. 2008, pp. 365-376.
U.S. Appl. No. 15/833,546, filed Dec. 6, 2017, by Blair et al.
READ, International Thermal Spray Association, Keynote address, China International Thermal Spray Conference and the 16th National Thermal Spraying Seminar, Dalian, China, Sep. 22-25, 2003, 68 pp.
Umeda et al., "On the sound sources of screech tones radiated from choked circular jets", The Journal of the Acoustical Society of America, vol. 110, No. 4, Oct. 2001, 14 pp.
Hou et al., "Acoustic Monitoring of Hydrocyclone Performance," Minerals Engineering, vol. 11, No. 11, Sep. 1998, pp. 1047-1059.

* cited by examiner

DIAGNOSIS OF THERMAL SPRAY GUN IGNITION

This application claims the benefit of U.S. Provisional Application No. 62/171,073, filed Jun. 4, 2015, which is incorporated by reference in its entirety.

TECHNICAL FIELD

The disclosure relates to thermal spray systems.

BACKGROUND

Thermal spray systems are used in a wide variety of industrial applications to coat substrates with coating material to modify or improve the properties of the target surface. Coatings may include thermal barrier coatings, hard wear coatings, ablative coatings, or the like. Thermal spray systems such as high velocity oxygen fuel (HVOF) systems introduce coating material in a plume so that molten particles propelled by the plume contact the surface of the target. Upon impact, the particles adhere to the target surface, resulting in a coating. A controlled ignition of a gas mixture may be used in HVOF systems to generate the plume.

SUMMARY

In some examples, the disclosure describes an example system including at least one acoustic sensor, a computing device, and an acoustic data signal processing module. The at least one acoustic sensor may be configured to generate at least one acoustic data signal indicative of an acoustic signal generated by a thermal spray system including a flowstream. Additionally, the acoustic data signal processing module may be operable by the computing device to determine an ignition attribute of the thermal spray system by analyzing at least a pre-ignition window of the acoustic data signal received by the computing device.

In some examples, the disclosure describes a technique that includes receiving, by a computing device, from at least one acoustic sensor, at least one acoustic data signal indicative of an acoustic signal generated by a thermal spray system comprising a flowstream. The computing device may determine an ignition attribute of the thermal spray system by analyzing at least a pre-ignition window of the acoustic data signal.

In some examples, the disclosure describes a computer readable storage medium includes instructions that, when executed, cause at least one processor to receive, from at least one acoustic sensor, at least one acoustic data signal indicative of an acoustic signal generated by a thermal spray system comprising a flowstream. The instruction also may cause the at least one processor to determine an ignition attribute of the thermal spray system by analyzing at least a pre-ignition window of the acoustic data signal.

The details of one or more examples are set forth in the accompanying drawings and the description below. Other features, objects, and advantages will be apparent from the description and drawings, and from the claims.

DETAILED DESCRIPTION

The disclosure describes systems and techniques for analyzing an acoustic signal of a flowstream flowing through a thermal spray gun to determine an ignition attribute of a flowstream. A thermal spray system may include at least one component, such as a spray gun, a powder feed system, a gas feed system, or like. During a thermal spray process, the spray gun may generate a spray by energizing the flowstream (for example, by subjecting the flowstream to plasma or ignition), subjecting spray material to the energized flowstream, which at least partially melts the spray material, and directing the at least partially melted spray material toward a spray target. The at least partially melted spray material contacts the spray target to form a coating of the spray material on the spray target. In HVOF systems, the flowstream may include oxygen and a fuel.

Various deviations in process parameters (e.g., temperature, pressure, flowrate, or composition of the flowstream) or system component conditions (gun nozzle wear, configuration of the spray gun) from nominal or designed values may lead to partial or complete failure of the spray process (e.g., ignition failure, intermittent ignition, or failure to satisfactorily melt or propel spray material). This may also lead to unsatisfactory coating characteristics, for instance, unsatisfactory coating thickness, composition, phase constitution, or the like. If an unsatisfactory ignition of the flowstream is detected, one or more of a shutdown, investigation, adjustment, correction, and restart of the flowstream may be utilized to avoid unsatisfactory coating of the coating target. However, unsatisfactory ignition may be difficult to detect, and restarting thermal spraying process may take undesirable amounts of time. Hence, predicting unsatisfactory ignition of the flowstream before the spraying is initiated, or determining unsatisfactory ignition soon after spraying is initiated, for instance, before introducing the powder feed into the energized flowstream, may reduce lost time due to the unsatisfactory ignition and resulting effects on the thermal spray process.

During operation of the thermal spray system, the flow of the flowstream through various system components may generate sound, which may be associated with thermal spray parameters, system component conditions, or both. In accordance with this disclosure, a thermal spray system may include at least one acoustic sensor configured to generate at least one acoustic data signal representative of the sound. The system also may include a computing device configured to analyze a pre-ignition window of the at least one acoustic data signal to determine whether an ignition attribute of the flowstream is within a nominal or expected range, or if the ignition attribute is different from an expected value. In some examples, the computing device additionally may determine occurrence of an ignition event and select the pre-ignition window based on the at least one acoustic data signal.

The thermal spray system described herein may perform real-time or near real-time analysis of the acoustic data signal, which may allow real-time or near real-time detection of the ignition attribute. In the event of an ignition failure, this may allow stopping or restarting of the thermal spray process early in the process, reducing or eliminating wasted time due to thermal spraying after ignition failure or poor ignition.

Figure 1:
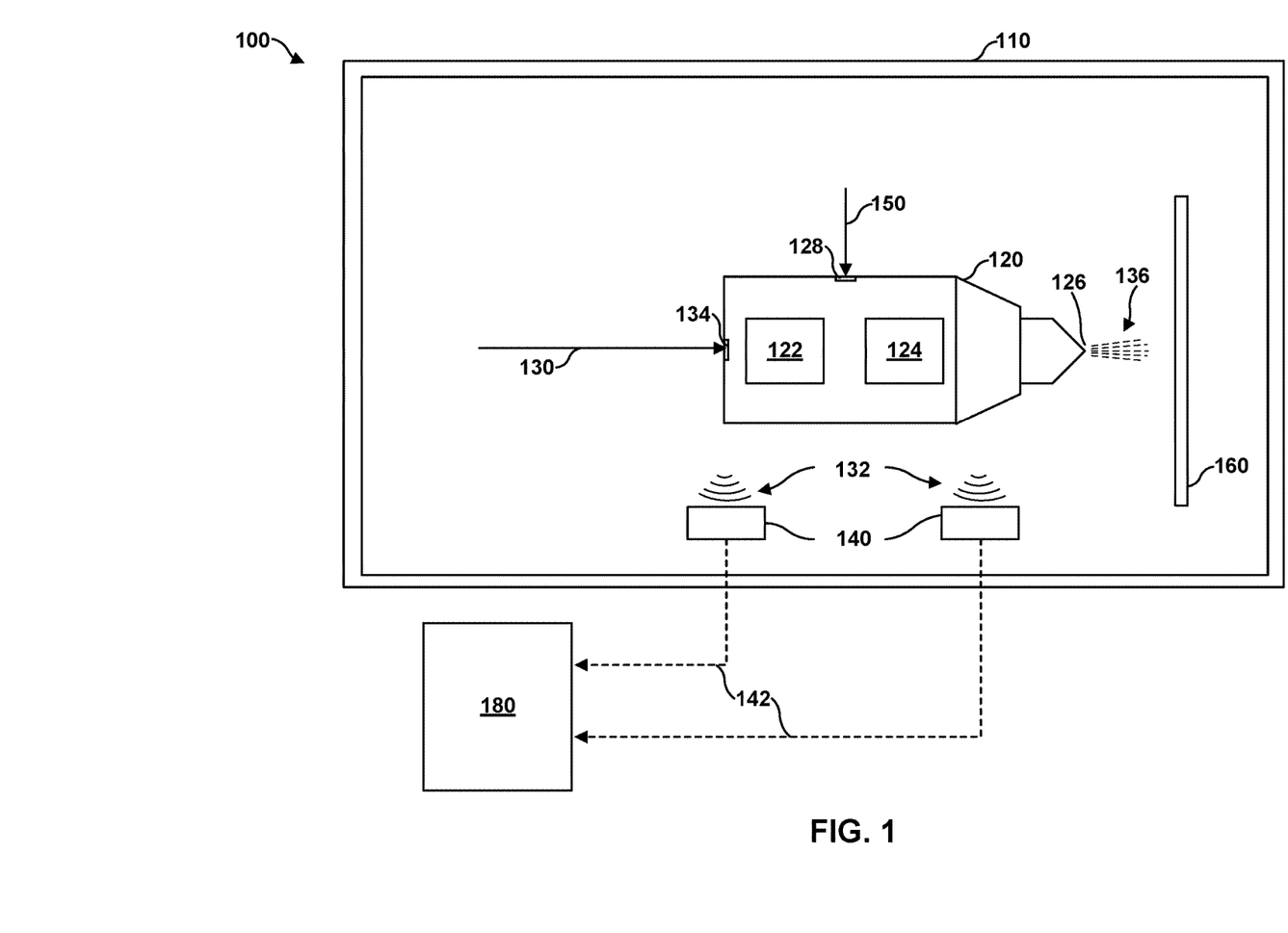
FIG. 1 is a conceptual block diagram illustrating an example thermal spray system including a flowstream, at least one acoustic sensor, and a computing device for analyzing an acoustic signal generated by the thermal spray system to determine an ignition attribute.

FIG. 1 is a block diagram illustrating an example thermal spray system 100. In some examples, thermal spray system 100 includes a high velocity oxygen fuel (HVOF) system. In some examples, thermal spray system 100 includes an enclosure 110, a thermal spray gun 120, at least one acoustic sensor 140, and a computing device 180.

Enclosure 110 encloses some components of thermal spray system 100, including, for example, thermal spray gun 120 and at least one acoustic sensor 140. In some examples, enclosure 110 substantially completely surrounds thermal spray gun 120 and at least acoustic sensor 140 and encloses an atmosphere. The atmosphere may include, for example, air, an inert atmosphere, a vacuum, or the like. In some examples, the atmosphere may be selected based on the type (e.g., composition) of coating being applied using thermal spray system 100. Enclosure 110 also encloses a spray target 160. In some examples, enclosure 110 includes a spray booth. In some example, computing device 180 is disposed within spray chamber 110. In some examples, computing device 180 is disposed outside spray chamber 110.

Spray target 160 includes a substrate to be coated using thermal spray system 100. In some examples, spray target 160 may include, for example, a substrate on which a bond coat, a primer coat, a hard coat, a wear-resistant coating, a thermal barrier coating, an environmental barrier coating, or the like is to be deposited. Spray target 160 may include a substrate or body of any regular or irregular shape, geometry, or configuration. In some examples, spray target 160 may include metal, plastic, glass, or the like. Spray target 160 may be a component used in any one or more mechanical systems, including, for example, a high temperature mechanical system such as a gas turbine engine.

Computing device 180 may be configured to control operation of one or more components of thermal spray system 100 automatically or under control of a user. For example, computing device 180 may be configured to control operation of thermal spray gun 120, gas feed line 130 (and the source of gas to gas feed line 130), material feed line 150 (and the source of material to material feed line 150), at least one acoustic sensor 140, and the like. Computing device 180 also may be configured to receive at least one acoustic data signal 142 from at least one acoustic sensor 140 and analyze the at least one acoustic data signal 142 to determine one or more process attributes of thermal spray system 100.

Thermal spray gun 120 is coupled to a spray material feed line 150 via material inlet port 128 and a gas feed line 130 via gas inlet port 134. Material feed line 150 may be coupled to a material source (not shown) that is located external to enclosure 110. Coating material may be fed through material feed line 150 in the form of one or more of a wire, a powder, a liquid, or a suspension, or the like, and may mix with gas from gas feed line 130 within thermal spray gun 120. The composition of the coating material may be based upon the composition of the coating to be deposited on spray target 160, and may include, for example, a metal, an alloy, a ceramic, or the like.

Gas feed line 130 provides a flowstream to gas inlet port 134 of thermal spray gun 120. Gas feed line 130 may be coupled to a gas source (not shown) that is external to enclosure 110. The flowstream may include oxygen and a fuel. In some examples, the fuel may include a liquid fuel, a vaporized liquid fuel, an atomized liquid fuel, a gaseous fuel, or a fuel otherwise combinable with oxygen to generate an ignitable mixture.

In some examples, thermal spray gun 120 includes a chamber 122 for subjecting spray material to the energized flowstream prior to spray outlet 126. In some examples, thermal spray gun 120 includes a plasma source and a plasma chamber for energizing the flowstream. In other examples, thermal spray gun 120 uses an ignition chamber to energize the flowstream by igniting and combusting the flowstream. In other examples, spray material may be introduced to the energized flowstream after exit flowstream 136 exits outlet 126. Outlet 126 of thermal spray gun 120 may be configured and positioned to direct the exit flowstream 136 including at least partially melted coating material at spray target 160.

As shown in FIG. 1, an exit flowstream 136 exits an outlet 126 of thermal spray gun 120. In some examples, outlet 126 includes a spray gun nozzle. In some examples, the flowstream is initially allowed to stabilize and exit unenergized through spray outlet 126, so that exit flowstream 136 initially includes the unenergized flowstream (with or without spray material). In examples, the composition, flow rate, temperature, or the like of the flowstream may change during the initial stabilization period.

In some examples, thermal spray system 100 may include an igniter 124, such as a spark plug or a lighter, for igniting flowstream 130. In some examples, thermal spray gun 120 includes igniter 124. In other examples, igniter 124 is external to thermal spray gun 120. Igniter 124 may be triggered manually or automatically to ignite flowstream 130, for instance, manually by an operator or automatically under control of computing device 180. After the flowstream is energized (for example, by subjecting it to plasma or combustion) exit flowstream 136 may initially include the energized flowstream (and not the coating material) or may include at least partially melted coating material carried by the energized flowstream. In some examples, the energized flowstream is allowed to stabilize before introducing the spray material. After introduction of the spray material, the energized flowstream partially, substantially, or completely melts the spray material. In some examples, after ignition, and after subjecting the spray material to the ignited flowstream, exit flowstream 136 may include, in addition to combustion products of the flowstream, semi-melted or melted particles, drops, droplets, globules, or other coat-providing forms of the spray material carried and propelled at relatively high velocities by the ignited flowstream in exit flowstream 136 towards spray target 160.

Thermal spray system 100 includes at least one acoustic sensor 140. In some examples, as shown in FIG. 1, thermal spray system 100 includes a plurality of acoustic sensors, such as at least two acoustic sensors 140. Each of the at least one acoustic sensor 140 is configured to sense acoustic signals 132 (e.g., sound). Acoustic signals 132 may be generated by one or more components or processes of thermal spray system 100, including thermal spray gun 120. The at least one acoustic sensor 140 may include, for example, may include an acoustic sensing element such as a microphone or a sound-to-electric transducer or electromagnetic, capacitive, or piezoelectric elements that generate an electrical signal in response to incident sound waves. The at least one acoustic sensor 140 may be configured to sense acoustic signals 132 with a predetermined wavelength or wavelength range. In some examples, the at least one acoustic sensor 140 may be configured to sense acoustic signals 132 that may or may not be detectable by human hearing, including infrasound and ultrasound. In various examples, acoustic signals 132 may include frequencies below about 20 Hz, from about 20 Hz to about 20 kHz, from about 20 kHz to about 2 MHz, higher than about 2 MHz, or combinations thereof. Each of the at least one acoustic sensor 140 is configured to generate a respective acoustic data signal 142 based on the sensed acoustic signal 132 and communicate the respective acoustic data signal 142 to computing device 180.

In examples, system 100 includes at least one amplifier or preamplifier for amplifying the electrical signals produced by the at least one acoustic sensor 140. For example, the at least one acoustic sensor 140 may include amplifiers. The at least one acoustic sensor 140 may transmit the acoustic data signal using electrical signals, Bluetooth, Wi-Fi, radio, or any other suitable transmission pathway. In some examples, some components of the at least one acoustic sensor 140 such as the acoustic sensing element, the data generating element, or the transmitter may be integrated into a single integrated circuit or chip or device. In some examples, the at least one acoustic sensor 140 may be configured, for instance, by situating, locating, orienting, or pointing to enhance detection of acoustic signals 132. In some examples, the at least one acoustic sensor 140 include an acoustic sensor network. In some examples, the at least one acoustic sensor 140 may include conductive leads or wireless transmitters for transmitting at least one acoustic data signal 142 in a manner receivable by computing device 180.

Thermal spray system 100 may generate different acoustic signals 132 during different stages of the thermal spray process, for instance, during startup, stabilization, spraying, and shutdown. For example, acoustic signals 132 may include frequencies exhibiting increased intensities across a number of frequency bands during an ignition event. In some examples, if ignition is not successful, incomplete, intermittent, or otherwise unsatisfactory, acoustic signals 132 may include frequencies that exhibit different intensities than those expected or associated with satisfactory ignition across at least one frequency band. In some examples, a variation in the flowstream through gas feed line 130 and exiting through spray outlet 126 may affect the velocity, viscosity, and density of the exit flowstream 136, which may lead to detectable changes in the frequency spectrum of acoustic signals 132, before, during, or after ignition. In some examples, acoustic signals 132 may differ when different types or configurations of thermal spray gun 120 or spray outlet 126 are used, for instance, when the wrong nozzle is used for the coating material being used, which may lead to unsatisfactory ignition.

Each of the at least one acoustic sensor 140 senses at least one of acoustic signals 132, and in response, generates at least one data signal 142. The at least one acoustic data signal 142 may be indicative of at least one of acoustic signals 132. In some examples, the at least one acoustic data signal 142 may be indicative of a superposition of acoustic signals 132. In some examples, the at least one acoustic sensors 140 may be active before ignition, or before and during ignition, or before, during, and after ignition.

The at least one acoustic data signal 142 includes at least a pre-ignition window. In some examples, the pre-ignition window may correspond to portions of acoustic signals 132 generated prior to an ignition event, for instance, ignition of the flowstream. In some examples, the pre-ignition window corresponds to a duration that includes about 5 seconds or about 3 seconds preceding ignition. In some examples, at least one acoustic data signal 142 also includes data representative of the ignition event.

Computing device 180 is configured to receive at least one acoustic data signal 142. Computing device 180 may be configured to analyze the pre-ignition window of at least one acoustic data signal 142 to determine an ignition attribute. Thus, in some examples, computing device 180 may determine an ignition attribute including at least one of satisfactory ignition, unsatisfactory ignition, or ignition failure, shortly after ignition is initiated or attempted, for instance, before spray material is introduced to thermal spray gun 120. In some examples, computing device 180 may determine the ignition attribute based on one of a peak frequency or a peak intensity (intensity of the peak frequency) within a selected frequency band. For example, the selected frequency band may include frequencies between about 3.8 kHz and about 4.4 kHz. In some examples, computing device 180 may compare one or both of peak frequency and peak intensity within the selected frequency band with a respective frequency threshold or frequency value and an intensity threshold or an intensity value to determine the ignition attribute. In some examples, computing device 180 determines the ignition attribute to include satisfactory ignition if the peak frequency is less than or equal to a frequency threshold value, and the peak intensity is greater than or equal to an intensity threshold value.

In this way, by utilizing at least one acoustic data signal 140, thermal spray system 100 described herein may perform real-time or near real-time analysis of at least one acoustic data signal 142, which may allow real-time or near real-time detection of the ignition attribute of thermal spray system 100. Further, monitoring a signal representative of the ignition attribute of thermal spray system 100 may provide a more accurate indication of an ignition attribute (for example, satisfactory ignition, unsatisfactory ignition, or ignition failure) of thermal spray system 100, e.g., compared to monitoring inputs to thermal spray system 100 using a flow meter, flow controller, amp meter, or voltmeter. Further, in some examples, flow meters, flow controllers, amp meters, and voltmeters may require calibration, and falling out of calibration may reduce the accuracy of the feedback provided by out-of-calibration flow meters, flow controllers, amp meters, and voltmeters.

Figure 2:
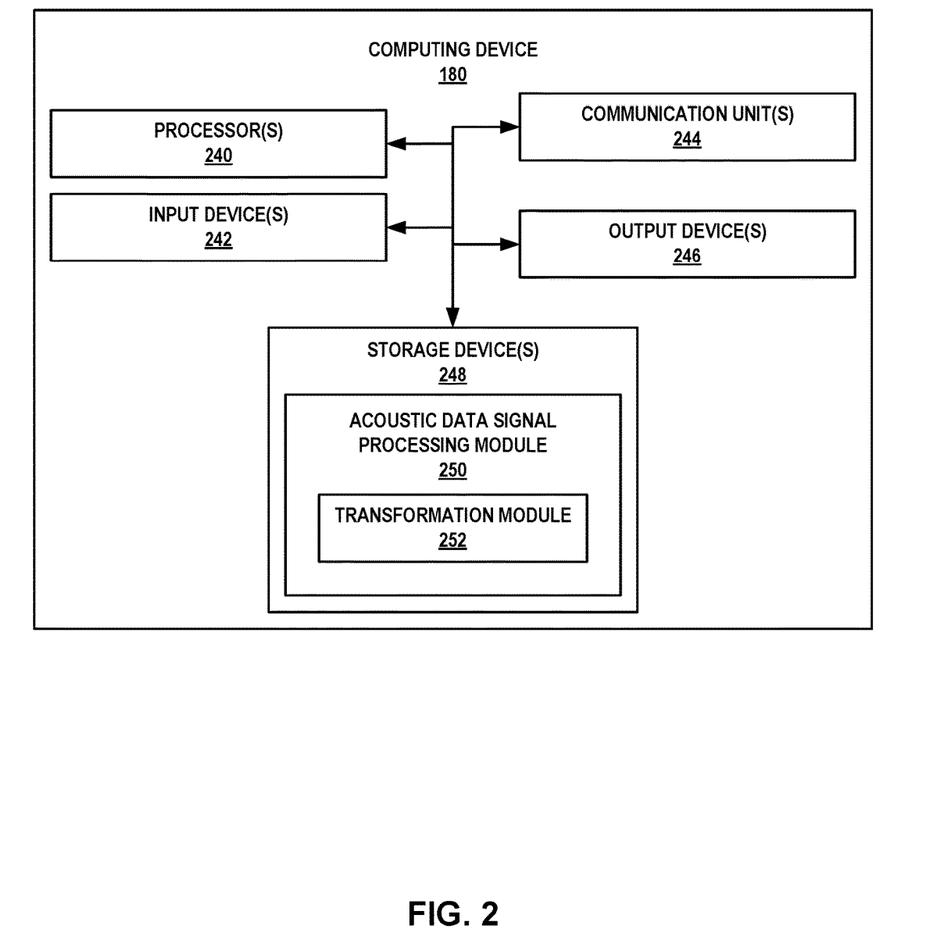
FIG. 2 is a conceptual block diagram illustrating an example of a computing device for analyzing an acoustic signal generated by a thermal spray system including a flowstream to determine an ignition attribute.

FIG. 2 is a conceptual block diagram illustrating an example of computing device 180 illustrated in FIG. 1. In some examples, computing device 180 may include, for example, a desktop computer, a laptop computer, a workstation, a server, a mainframe, a cloud computing system, or the like. In some examples, computing device 180 controls the operation of system 100, including, for example, thermal spray gun 120, gas feed line 130, gas inlet port 134, exit flowstream 136, the at least one acoustic sensor 140, spray material feed 150, material inlet port 128, and spray target 160.

In the example illustrated in FIG. 2, computing device 180 includes one or more processors 240, one or more input devices 242, one or more communication units 244, one or more output devices 246, and one or more storage devices 248. In some examples, one or more storage devices 248 stores acoustic data signal processing module 250, which includes transformation module 252. In other examples, computing device 180 may include additional components or fewer components than those illustrated in FIG. 2.

One or more processors 240 are configured to implement functionality and/or process instructions for execution within computing device 180. For example, processors 240 may be capable of processing instructions stored by storage device 248. Examples of one or more processors 40 may include, any one or more of a microprocessor, a controller, a digital signal processor (DSP), an application specific integrated circuit (ASIC), a field-programmable gate array (FPGA), or equivalent discrete or integrated logic circuitry.

One or more storage devices 248 may be configured to store information within computing device 180 during operation. Storage devices 248, in some examples, include a computer-readable storage medium or computer-readable storage device. In some examples, storage devices 248 include a temporary memory, meaning that a primary purpose of storage device 248 is not long-term storage. Storage devices 248, in some examples, include a volatile memory, meaning that storage device 248 does not maintain stored contents when power is not provided to storage device 248. Examples of volatile memories include random access memories (RAM), dynamic random access memories (DRAM), static random access memories (SRAM), and other forms of volatile memories known in the art. In some examples, storage devices 248 are used to store program instructions for execution by processors 240. Storage devices 248, in some examples, are used by software or applications running on computing device 180 to temporarily store information during program execution.

In some examples, storage devices 248 may further include one or more storage device 248 configured for longer-term storage of information. In some examples, storage devices 248 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Computing device 180 further includes one or more communication units 244. Computing device 180 may utilize communication units 244 to communicate with external devices (e.g., thermal spray gun 120, gas feed line 130, gas inlet port 134, exit flowstream 136, at least one acoustic sensor 140, material feed 150, material inlet port 128, and spray target 160) via one or more networks, such as one or more wired or wireless networks. Communication unit 244 may include a network interface card, such as an Ethernet card, an optical transceiver, a radio frequency transceiver, or any other type of device that can send and receive information. In some examples, the communication connections may include network links, such as Ethernet, ATM, or other network connections. Such connections may be wireless and/or wired connections. In other examples, the communication connections may include other types of device connections, such as USB, IEEE 1394, or the like. Other examples of such network interfaces may include WiFi radios or Universal Serial Bus (USB). In some examples, computing device 180 utilizes communication units 244 to wirelessly communicate with an external device such as a server.

Computing device 180 also includes one or more input devices 242. Input devices 242, in some examples, are configured to receive input from a user through tactile, audio, or video sources. Examples of input devices 242 include a mouse, a keyboard, a voice responsive system, video camera, microphone, touchscreen, or any other type of device for detecting a command from a user.

Computing device 180 may further include one or more output devices 246. Output devices 46, in some examples, are configured to provide output to a user using audio or video media. For example, output devices 246 may include a display, a sound card, a video graphics adapter card, or any other type of device for converting a signal into an appropriate form understandable to humans or machines. In some examples, computing device 180 outputs at least one of an alert or a representation of the at least one acoustic data signal 142, the ignition attribute, the frequency-domain spectrum, or a spectrogram, via output devices 246.

In some examples, computing device 180 may generate an alert in response to the least one attribute, via output devices 246. In some examples, computing device 180 may generate auditory signals, such as a beep, an alert tone, or an alerting sound, or visual signals, such as an icon on a display, flashing lights, or a combination of visual and audible signals, to indicate an unsatisfactory ignition. In some examples, an operator may thus be alerted, and may choose to investigate system 100. In another example, computing device 180 may generate an alert in the form of an alert signal transmitted over a network to another computing device, including a hand-held computing device, for instance, a cellphone. The alert signal may include information about the attribute, for instance, the ignition quality.

Computing device 180 also may include acoustic data signal processing module 250, which includes transformation module 252. Acoustic data signal processing module 250 and transformation module 252 may be implemented in various ways. For example, acoustic data signal processing module 250, transformation module 252, or both may be implemented as software, such as an executable application or an operating system, or firmware executed by one or more processors 240. In other examples, acoustic data signal processing module 250, transformation module 252, or both may be implemented as part of a hardware unit of computing device 200. Functions performed by acoustic data signal processing module 250 and transformation module 252 are explained below with reference to the example flow diagram illustrated in FIG. 3.

Computing device 180 may include additional components that, for clarity, are not shown in FIG. 2. For example, computing device 180 may include a power supply to provide power to the components of computing device 180. Similarly, the components of computing device 180 shown in FIG. 2 may not be necessary in every example of computing device 180.

Examples of thermal spray system 100 and computing device 180 are described with reference to FIGS. 1 and 2 above, including examples of at least one acoustic sensor 140 for generating at least one acoustic data signal 142 indicative of acoustic signals 132 generated by thermal spray system 100. Example techniques for analyzing at least one data signals to determine an ignition attribute of are described with reference to FIG. 3 below.

Figure 3:
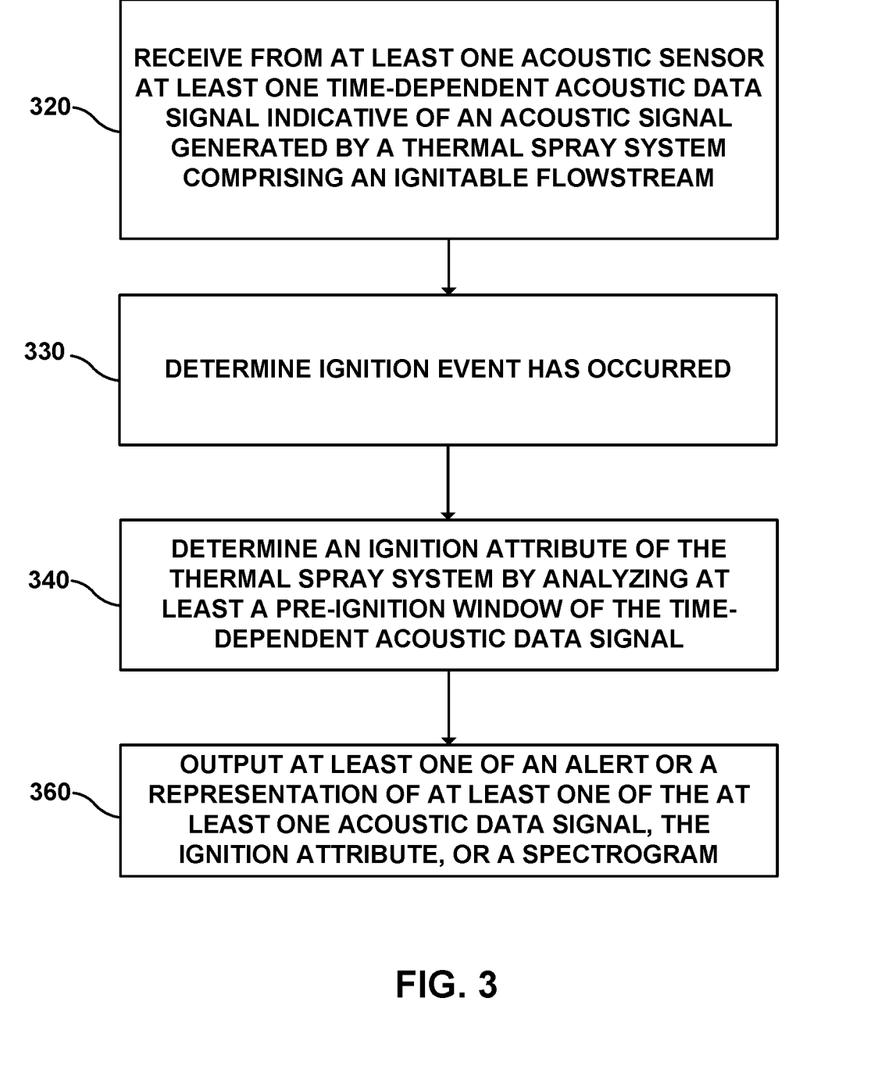
FIG. 3 is a flow diagram illustrating an example technique for analyzing an acoustic signal generated by a thermal spray system including a flowstream to determine an ignition attribute.

FIG. 3 is a flow diagram illustrating an example technique for analyzing an acoustic signal generated by a thermal spray system including a flowstream to determine an ignition attribute. In some examples, a computing device, such as computing device 180, may implement the technique of FIG. 3 to analyze the at least one acoustic data signal 142 indicative of acoustic signals 132 generated by thermal spray system 100 described in various examples with reference to FIG. 1. The technique of FIG. 3 will be described with reference to thermal spray system 100 of FIG. 1, and computing device 180 of FIGS. 1 and 2, for purposes of description only. It will be appreciated that the technique of FIG. 3 may be used to analyze at least one acoustic data signal to determine an ignition attribute of other thermal spray systems, that other computing devices may implement the technique of FIG. 3, or both.

The technique of FIG. 3 includes receiving, by computing device 180, from at least one acoustic sensor 140, at least one acoustic data signal 142 indicative of acoustic signals 132 generated by thermal spray system (320). In some examples, at least one acoustic data signal 142 may include analog signals and acoustic data signal processing module 250 of computing device 180 may process the at least one acoustic data signal 142 by performing an analog-to-digital conversion. In other examples, the received at least one acoustic data signal 142 may include digital signals and no analog-to-digital conversion may be performed. In some examples, acoustic data signal processing module 250 may filter at least one acoustic data signal 142 through at least one signal processing filter such as band pass filters, high pass filters, low pass filters, comb filters, notch filters, or other filters, for instance, deconvolution filters or noise filters to select one or more frequency bands of at least one acoustic data signal 142, filter out undesirable signal components, such as noise, superfluous signal components, such as harmonics, or to reduce or compress the information in at least one acoustic data signal 142.

In some examples, transformation module 252 of computing device 180 may transform at least one acoustic data signal 142 to a frequency-domain spectrum by extracting frequency and corresponding intensity components of at least one acoustic data signal 142 and identifying intensity as a function of frequency. For example, transformation module 252 may transform at least one acoustic data signal 142 from the time domain to the frequency-domain using at least one of a fast Fourier transform or a discrete Fourier transform. Transformation module 252 of computing device 180 may perform the transformation before, during, or after other processing of at least one acoustic data signal 142, such as filtering described above. In some examples, computing device 180 may perform at least some of the subsequent processing of at least one acoustic data signal 142 described herein in the frequency-domain.

In some examples, the technique of FIG. 3 optionally includes determining, by acoustic data signal processing module 250 of computing device 180, that an ignition event has occurred (330). For example, at least one acoustic data signal 142 may include signals generated before, during and after ignition, and acoustic data signal processing module 250 may identify the ignition event by analyzing at least one acoustic data signal 142.

In some examples, acoustic data signal processing module 250 may identify an ignition event by at least comparing intensities of a plurality of frequencies to respective threshold intensity values. The plurality of frequencies may include frequencies distributed across multiple frequency bands in an expected frequency spectrum (e.g., including frequencies from a known lower frequency range, a known central frequency range, and a known higher frequency range). In some examples, acoustic data signal processing module 250 may identify an ignition event by determining that at least some, a majority, or substantially all of the frequencies of the plurality of frequencies exhibit respective intensities greater than or equal to the respective threshold intensity values.

In some examples, acoustic data signal processing module 250 may transform an ignition check window of at least one acoustic data signal 142 received at time t to a frequency-domain spectrum and identify whether an ignition event occurred within the ignition check window by analyzing the frequency-domain spectrum of the ignition check window. In some examples, each ignition check window has a predetermined duration, and acoustic data signal processing module 250 may select ignition check windows periodically and analyze the respective ignition check windows to determine if an ignition event occurred during the selected ignition check window. In some examples, computing device 180 selects adjacent, abutting, or overlapping ignition check windows from at least one acoustic data signal 142, so that at least one ignition check window of the series of ignition check windows includes an ignition event.

Acoustic data signal processing module 250 may analyze ignition check windows received at each time interval t to identify if an ignition event occurred within an ignition check window. In some examples, if acoustic data signal processing module 250 identifies an ignition event within an ignition check window, acoustic data signal processing module 250 may select a portion of at least one acoustic data signal 142 preceding that ignition check window as the pre-ignition window. In some examples, acoustic data signal processing module 250 may select about 3 seconds of at least one acoustic data signal 142 immediately preceding the ignition event as the pre-ignition window.

In other examples, acoustic data signal processing module 250 may not determine an ignition event based on at least one acoustic data signal 142. Instead, in some examples, computing device 180 may identify the time stamp of the ignition event by analyzing a non-acoustic data signal, for instance, by analyzing an optical, electrical, or other signal, and may select the pre-ignition window by selecting a portion of at least one signal 142 preceding a time stamp of the ignition event. In some examples, a device other than computing device 180 may detect the ignition event, for instance, by analyzing an acoustic, optical, electrical, or other signal and send the time-stamp of the ignition event to computing device 180, so that acoustic data signal processing module 250 can select the pre-ignition window of at least one acoustic data signal 142 based on the time-stamp. In some examples, the pre-ignition window may be identified by another device, and only the pre-ignition window of at least one acoustic data signal 142 may be provided to computing device 180.

Regardless of the technique by which the pre-ignition window is identified, the technique of FIG. 3 also includes determining, by acoustic data signal processing module 250 of computing device 180, an ignition attribute of thermal spray system 100 by analyzing at least a pre-ignition window of acoustic data signal 142 (340).

In examples in which transform module 252 transforms at least one acoustic data signal 142 from the time domain to the frequency-domain, acoustic data signal processing module 250 of computing device 180 may analyze the frequency-domain spectrum to determine the ignition attribute. For example, signal processing module 250 of computing device 180 may select a frequency band (e.g., a predetermined frequency band) using a filter, such as a band pass filter, or another technique. The frequency band may be selected to include frequencies representative of ignition attributes, which may be determined, e.g., using experimentation. For example, the selected frequency band comprises frequencies from about 3.8 kHz to about 4.5 kHz.

Acoustic data signal processing module 250 may extract one or both of a peak intensity and a peak frequency from the selected frequency band to determine the ignition attribute. In some examples, acoustic data signal processing module 250 may compare the peak intensity within the frequency band with an intensity threshold value or an intensity range, may compare the peak frequency within the frequency band with a frequency threshold value or range to determine the ignition attribute.

In some examples, acoustic data signal processing module 250 may identify the peak intensity within the frequency band by identifying the maximum intensity from all intensities of respective frequencies within the selected frequency band. In some examples, acoustic data signal processing module 250 may determine the ignition attribute to include satisfactory ignition if the peak intensity is greater than or equal to a predetermined intensity threshold, and unsatisfactory ignition if the peak intensity is less than the predetermined intensity threshold. In some examples, acoustic data signal processing module 250 may determine the ignition attribute to include ignition failure if the peak intensity is very small compared to the predetermined intensity threshold, for instance, if the peak intensity is less than 10%, or less than 5%, or less than 1%, or less than 0.1% of the predetermined intensity threshold.

In some examples, acoustic data signal processing module 250 may identify the peak frequency within the selected frequency band by identifying the frequency at which the frequency band exhibits the maximum or peak intensity. Acoustic data signal processing module 250 may compare the peak frequency within the selected frequency band with a frequency threshold value to determine the ignition attribute. For example, acoustic data signal processing module 250 may determine the ignition attribute to include unsatisfactory ignition if the peak frequency is greater than or equal to a predetermined frequency threshold, and satisfactory ignition if the peak frequency is less than the predetermined intensity threshold. In some examples, acoustic data signal processing module 250 may compare the peak frequency within the selected frequency band with a predetermined frequency range to determine the ignition attribute. For example, acoustic data signal processing module 250 may determine the ignition attribute to include satisfactory ignition if the peak frequency is within the predetermined frequency range and unsatisfactory ignition if the peak frequency is outside the predetermined frequency range.

In some examples, in addition to distinguishing between satisfactory ignition events and ignition failure, acoustic signals 132 may indicate that thermal spray gun 120 is being used with an inappropriate coating material. For example, acoustic signals 132, and consequently, at least one acoustic data signal 142, may differ when different types or configurations of thermal spray gun 120 or spray outlet 126 are used. For example, acoustic signals 132, and consequently, at least one acoustic data signal 142, may differ when the wrong nozzle is used for the coating material being used. In some examples, a gun mismatch may result in a change in at least one of peak frequency or peak intensity within a selected frequency band compared to the peak frequency and peak intensity exhibited when the thermal spray gun is matched with or appropriate for the spray material or the parameters of the thermal spray process. In response to receiving at least one acoustic data signal 142 from a configuration in which thermal spray gun 120 is not matched with the coating material or coating process parameters, acoustic data signal processing module 250 may determine the ignition attribute to include a gun mismatch. In some examples, acoustic data signal processing module 250 may determine a mismatch if the peak intensity is greater than or equal to a predetermined mismatch intensity threshold, if the peak frequency is greater than or equal to a predetermined mismatch frequency threshold, or both. In some examples, the mismatch frequency threshold may be 3.9 kHz.

In some examples, as described above, at least one processor 240 may control output devices 246 to output at least one of an alert or a representation of at least one of at least one acoustic data signal 142, the ignition attribute, or a spectrogram (360). In some examples, at least one processor 240 may control output devices 246 to output the alert in a visual form, for instance, as an icon or a pop-up message at a display. In some examples, at least one processor 240 may control output devices 246 to output the alert in an audible form played through a speaker. In some examples, at least one processor 240 may control at least one communication unit 244 to transmit a signal indicating an alert to a second computing device, over a wired or wireless communication channel, for instance to a wall-mounted device, a hand-held device, or a peripheral that may output the alert. In some examples, at least one processor 240 may control output devices 246 to output the alert as a tactile signal, for instance, a vibration-based alert.

In some examples, the techniques described with reference to FIG. 3 may be implemented as real-time, near real-time, or online processes, so that computing device 180 generates an alert relatively immediately if the ignition attribute includes unsatisfactory ignition or ignition failure. In some examples, the techniques may be implemented as an offline process or a post-processing diagnostic tool, so that computing device 180 diagnoses a past ignition attribute.

In some examples, computing device 180 may determine imminent shutdown of thermal spray system 100 when intensities substantially decrease across a majority of or substantially all of the plurality of frequencies.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer system-readable medium, such as a computer system-readable storage medium, containing instructions. Instructions embedded or encoded in a computer system-readable medium, including a computer system-readable storage medium, may cause one or more programmable processors, or other processors, to implement one or more of the techniques described herein, such as when instructions included or encoded in the computer system-readable medium are executed by the one or more processors. Computer system readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media. In some examples, an article of manufacture may comprise one or more computer system-readable storage media.

EXAMPLES

Example 1

Figure 4:
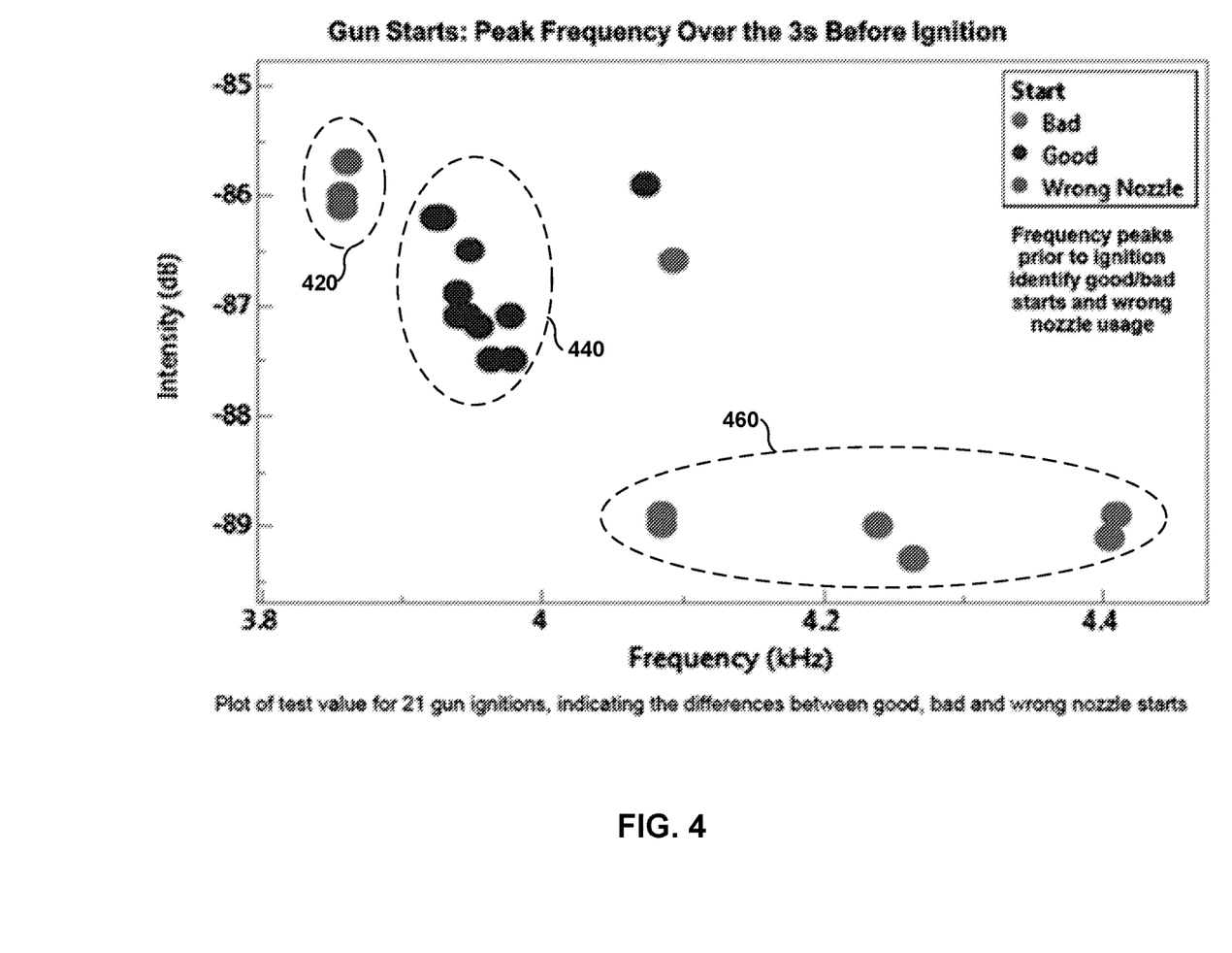
FIG. 4 is a chart presenting a plot of peak frequencies and intensities associated with example ignition events.

FIG. 4 is a chart illustrating a plot of peak frequencies and intensities associated with example ignition events. 21 ignition events were monitored, and the peak frequencies and intensities identified within a selected frequency band of 3.8 kHz to 4.5 kHz. Satisfactory ignition events 440 exhibited peak frequencies of more than about 3.9 kHz and less than about 4 kHz and intensities greater than about −88 dB. Unsatisfactory ignition events 460 exhibited peak frequencies of greater than about 4 kHz and intensities less than about −88 dB. Mismatched ignition events 420 associated with using the wrong nozzle or mismatched gun type for the spray material exhibited peak frequencies of less than about 3.9 kHz.

Various examples have been described. These and other examples are within the scope of the following claims.

The invention claimed is:

1. A system comprising: at least one acoustic sensor configured to generate at least one acoustic data signal indicative of an acoustic signal generated by a thermal spray system comprising a flowstream; a computing device comprising at least one processor; an acoustic data signal processing module operable by the at least one processor to determine an ignition attribute of the thermal spray system by analyzing at least a pre-ignition window of the acoustic data signal received by the computing device by at least: transforming the at least one acoustic data signal associated with the pre-ignition window to a frequency-domain spectrum, and comparing a peak intensity within a selected frequency band of the frequency-domain spectrum with a predetermined intensity range for the selected frequency band to determine the ignition attribute of the thermal spray system; and an output device configured to output at least one of an alert or a representation of at least one of the at least one acoustic data signal, the ignition attribute, or a spectrogram associated with the pre-ignition window, wherein the computing device is configured to, in response to determining that the ignition attribute is indicative of ignition failure or improper ignition, stop or restart a thermal spray process performed by the thermal spray system by sending a control signal to the thermal spray system before introducing spray material into the flowstream.

2. The system of claim 1, wherein the ignition attribute comprises at least one of a satisfactory ignition, an unsatisfactory ignition, and an ignition failure.

3. The system of claim 1, wherein the acoustic data signal processing module is further operable by the at least one processor to transform the at least one acoustic data signal to the frequency-domain spectrum using at least one of a discrete Fourier transform or a fast Fourier transform.

4. The system of claim 1, wherein the acoustic data signal processing module is operable by the at least one processor to identify an ignition event by at least comparing intensities of a plurality of frequencies to respective threshold intensity values and selecting a portion of the at least one acoustic data signal preceding the ignition event as the pre-ignition window.

5. The system of claim 1, wherein the acoustic data signal processing module is operable by the at least one processor to compare a peak frequency within the selected frequency band with a predetermined frequency range to determine the ignition attribute of the thermal spray system.

6. The system of claim 1, wherein the selected frequency band comprises frequencies from about 3.8 kHz to about 4.5 kHz.

7. The system of claim 1, wherein the pre-ignition window comprises less than about 3 seconds of the at least one acoustic data signal preceding the ignition event.

8. A method comprising: receiving, by a computing device, from at least one acoustic sensor, at least one acoustic data signal indicative of an acoustic signal generated by a thermal spray system comprising a flowstream; determining, by the computing device, an ignition attribute of the thermal spray system by analyzing at least a pre-ignition window of the acoustic data signal by at least: transforming the at least one acoustic data signal to a frequency-domain spectrum, and comparing a peak intensity within a selected frequency band with a predetermined intensity range for the selected frequency band; causing, by the computing device, an output device to output at least one of an alert or a representation of at least one of the at least one acoustic data signal, the ignition attribute, or a spectrogram; and causing, by the computing device, in response to determining that the ignition attribute is indicative of ignition failure or improper ignition, stop or restart a thermal spray process performed by the thermal spray system by sending a control signal to the thermal spray system before introducing spray material into the flowstream.

9. The method of claim 8, wherein the ignition attribute comprises at least one of a satisfactory ignition, an unsatisfactory ignition, and an ignition failure.

10. The method of claim 8, wherein determining the ignition attribute comprises transforming, by the computing device, the at least one acoustic data signal to the frequency-domain spectrum using at least one of a fast Fourier transform or a discrete Fourier transform.

11. The method of claim 8, wherein determining the ignition attribute comprises comparing a peak frequency within the selected frequency band with a predetermined frequency range.

12. The method of claim 8, wherein the selected frequency band comprises frequencies from about 3.8 kHz to about 4.5 kHz.

13. The method of claim 8, wherein the pre-ignition window comprises less than about 3 seconds of the at least one acoustic data signal preceding the ignition event.

14. The method of claim 8, wherein the analyzing comprises identifying an ignition event by at least comparing intensities of a plurality of frequencies to respective threshold intensity values and selecting a portion of the at least one acoustic data signal preceding the ignition event as the pre-ignition window.

15. A non-transitory computer readable storage medium comprising instructions that, when executed, cause at least one processor to: receive, from at least one acoustic sensor, at least one acoustic data signal indicative of an acoustic signal generated by a thermal spray system comprising a flowstream; determine an ignition attribute of the thermal spray system by analyzing at least a pre-ignition window of the acoustic data signal by at least: transforming the at least one acoustic data signal associated with the pre-ignition window to a frequency-domain spectrum, and comparing a peak intensity within a selected frequency band of the frequency-domain spectrum with a predetermined intensity range for the selected frequency band to determine the ignition attribute of the thermal spray system; cause an output device to output at least one of an alert or a representation of at least one of the at least one acoustic data signal, the ignition attribute, or a spectrogram; and cause, in response to determining that the ignition attribute is indicative of ignition failure or improper ignition, stop or restart a thermal spray process performed by the thermal spray system by sending a control signal to the thermal spray system before introducing spray material into the flowstream.

16. The non-transitory computer readable medium of claim 15, further comprising instructions, that when executed, cause the at least one processor to:
  transform the at least one acoustic data signal to the frequency-domain spectrum using at least one of a fast Fourier transform or a discrete Fourier transform, and
  determine the ignition attribute by at least comparing a peak frequency within the selected frequency band with a predetermined frequency range.

* * * * *